United States Patent [19]

Frisbie et al.

[11] Patent Number: 4,664,113

[45] Date of Patent: May 12, 1987

[54] STEERABLE DILATATION CATHETER WITH ROTATION LIMITING DEVICE

[75] Inventors: Jeffrey S. Frisbie, San Jose; Wilfred J. Samson, Saratoga; John V. Hoek, Wildomar, all of Calif.

[73] Assignee: Advanced Cardiovascular Systems, Inc., Mountain View, Calif.

[21] Appl. No.: 760,635

[22] Filed: Jul. 30, 1985

Related U.S. Application Data

[63] Continuation-in-part of Ser. No. 615,118, May 30, 1984, abandoned.

[51] Int. Cl.⁴ .............................................. A61M 29/02
[52] U.S. Cl. .................................... 128/344; 128/657; 128/772; 604/96
[58] Field of Search ............... 128/344, 343, 772, 657; 604/95–102, 164, 165, 171

[56] References Cited

U.S. PATENT DOCUMENTS

| | | | |
|---|---|---|---|
| 3,503,385 | 3/1970 | Stevens | 128/657 |
| 3,552,384 | 1/1971 | Pierie et al. | 128/657 |
| 3,773,034 | 11/1973 | Burns | 604/95 |
| 4,292,974 | 10/1981 | Fogarty et al. | 604/98 |
| 4,332,254 | 6/1982 | Lundquist | 128/344 |
| 4,338,942 | 7/1982 | Fogarty et al. | 604/99 |
| 4,403,612 | 9/1983 | Fogarty et al. | 128/344 |
| 4,422,447 | 12/1983 | Schiff | 128/344 |

Primary Examiner—Robert P. Swiatek
Assistant Examiner—Cary E. Stone
Attorney, Agent, or Firm—Flehr, Hohbach, Test, Albritton & Herbert

[57] ABSTRACT

Steerable dilatation catheter assembly having an adapter with at least one arm. A guide wire having proximal and distal ends is provided with the proximal end extending through the adapter. A flexible tubular member has one end secured to the adapter and extends over the guide wire and has a balloon carried by a distal portion thereof. The distal extremity of the balloon is bonded to the guide wire to form a liquid-tight seal between the guide wire and the balloon. A flexible tip is secured to the guide wire. A rotation limiter secured to the guide wire and carried by the arm for rotating the guide wire through a number of turns less than a predetermined number of turns.

18 Claims, 7 Drawing Figures

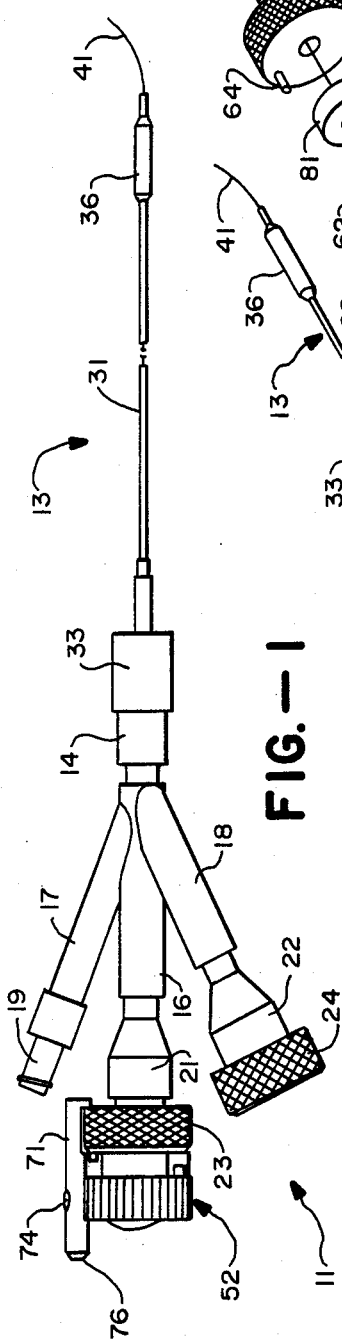
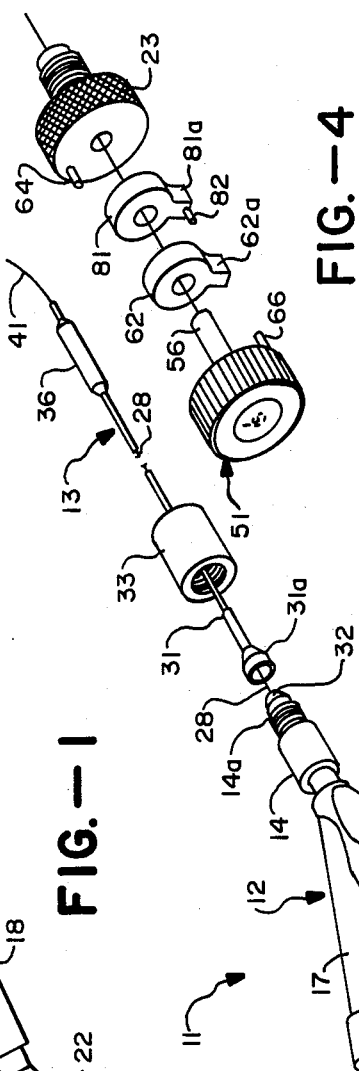
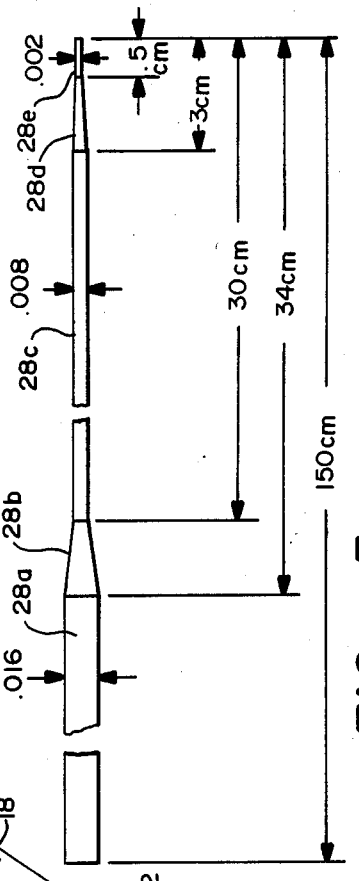
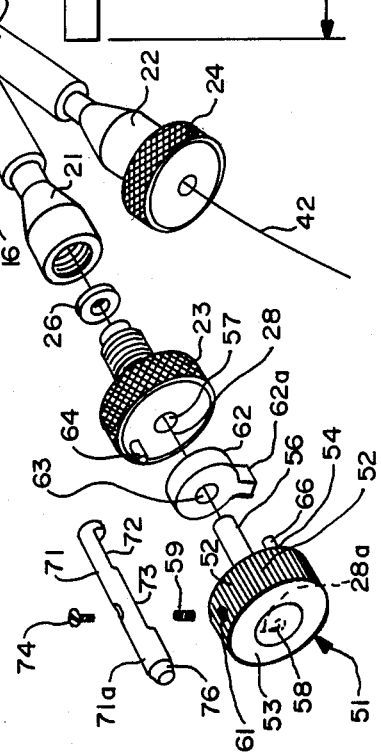
U.S. Patent  May 12, 1987  Sheet 1 of 2  4,664,113
FIG.—1
FIG.—2
FIG.—3
FIG.—4

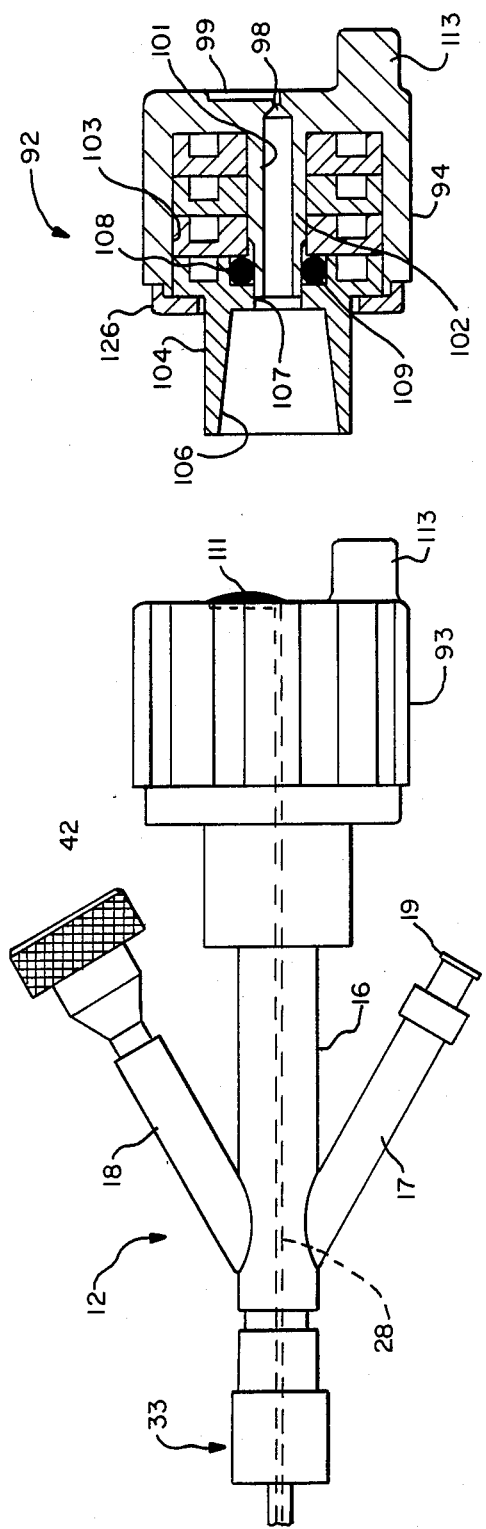
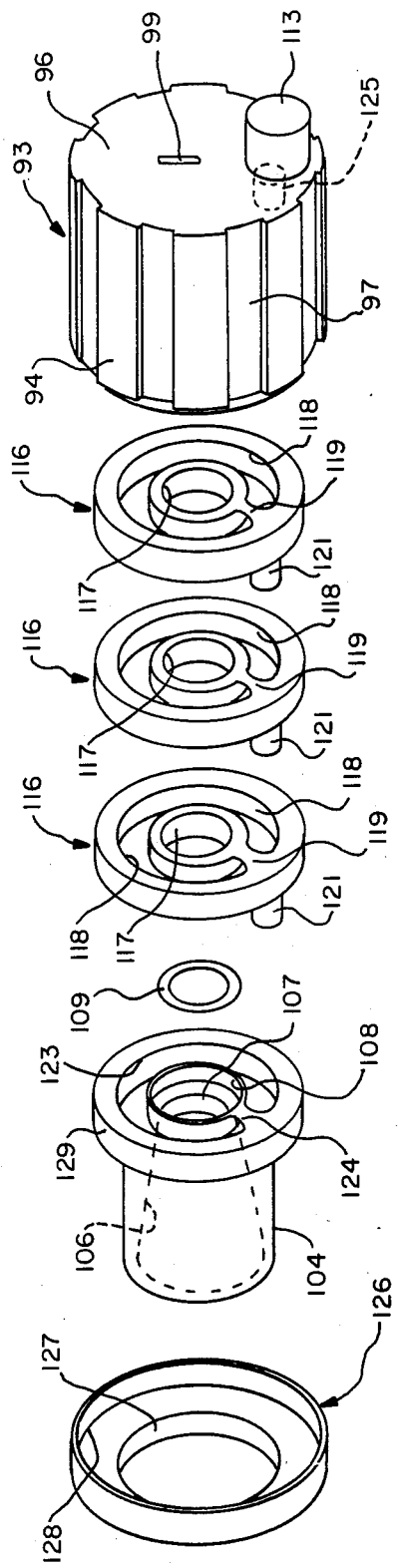

STEERABLE DILATATION CATHETER WITH ROTATION LIMITING DEVICE

This application is a continuation-in-part of application Ser. No. 615,118 filed May 30, 1984 now abandoned.

This application relates to a steerable dilatation catheter assembly with a rotation limiting device and more particularly, to a low profile steerable dilatation catheter with a rotation limiting device.

In co-pending application Ser. No. 522,835 filed on Aug. 12, 1983, now U.S. Pat. No. 4,582,181, there is disclosed a steerable dilatation catheter. Difficulties have been encountered with this catheter in that surgeons using the same have rotated the guide wire to such an extent that the balloon has been twisted making it difficult to inflate. There is therefore a need for a new and improved steerable dilatation catheter which will overcome this difficulty.

In general, it is an object of the present invention to provide a low profile steerable dilatation catheter which makes it more difficult to twist the balloon.

Another object of the invention is to provide a catheter assembly of the above character in which the guide wire has greater torsional capabilities.

Another object of the invention is to provide a catheter assembly of the above character in which the number of turns the guide wire is rotated is limited to a predetermined number of revolutions.

Another object of the invention is to provide a catheter assembly of the above character in which fingertip control for rotation of the guide wire is provided.

Another object of the invention is to provide a catheter assembly of the above character which prevents accidental retraction of the guide wire.

Another object of the invention is to provide a catheter assembly of the above character which makes it possible to limit the amount of rotation of the guide wire while still obtaining one turn of the tip in response to the limited rotation.

Additional objects and features of the invention will appear from the following description in conjunction with the accompanying drawings.

FIG. 1 is a side elevational view of a low profile dilatation catheter assembly with a rotation limiting device incorporating the present invention.

FIG. 2 is a partially exploded view of the catheter assembly shown in FIG. 1.

FIG. 3 is an enlarged side elevational view of the core wire used in the catheter assembly.

FIG. 4 is an exploded view of a catheter assembly of the type shown in FIG. 2 which permits three turns of the core wire at the proximal extremity while providing only one turn of the tip.

FIG. 5 is a partial side elevational view of another embodiment of a catheter assembly with a rotation limiting device incorporating the present invention.

FIG. 6 is a cross sectional view of the rotation limiting device shown in FIG. 5.

FIG. 7 is an exploded view of the rotation limiting device shown in FIG. 6.

In general, the low profile steerable dilatation catheter assembly is comprised of a guide wire having proximal and distal ends. An adapter is provided with at least one arm having the guide wire extending therethrough. An elongate flexible tubular member extends over the guide wire from the adapter to a region near the distal extremity of the guide wire. A flexible tip is carried by the guide wire. The tubular member carries an inflatable balloon that has its distal extremity secured to the core wire so as to provide a liquid-tight seal.

A rotation limiting device is carried by the arm of the adapter. The rotating limiting device includes a rotatable member and means securing the guide wire to the rotatable member. Means is also provided which engages the rotatable member for preventing rotation of the rotatable member for more than a predetermined number of turns.

More particularly as shown in FIG. 1, the low profile steerable dilatation catheter assembly with rotation limiting device 11 consists of an adapter 12 which is connected to a catheter 13. The adapter 12 is provided with a body 14 which carries a central arm 16 and two side arms 17 and 18. The side arm 17 is provided with a Luer fitting 19 which is adapted to be connected to means for introducing a radiopaque contrast liquid into the side arm 17. Such a device can take the form disclosed in U.S. Pat. No. 4,439,185. The central arm 16 and the side arm 17 have receptacles 21 and 22 carried thereby which are internally threaded. The receptacles 21 and 22 are adapted to receive thumb screws 23 and 24 which are threaded therein. Means is provided within each of the receptacles 21 and 22 for establishing a liquid tight seal and takes the form of an O-ring 26 which is adapted to be engaged by the thumb screw 23 to be forced into the receptacle to form a sealing engagement.

A core or guide wire 28 is provided and extends through the central arm 16. The core or guide wire 28 is formed of a suitable material such as stainless steel. Typically such a core wire can have a length of approximately 150 centimeters. In order to obtain the desired torsional rigidity, the core or guide wire 28 is preferably solid. It is circular in cross section and has a diameter which is substantially greater than 0.013 of an inch as, for example, 0.016 of an inch. The core wire has this dimension substantially throughout its entire length as represented by portion 28a. At a region which is close to the distal extremity of the core wire, for example, at a distance of from 30 to 40 centimeters and preferably approximately 34 centimeters, the core wire necks down in portion 28b to a smaller diameter to provide a conical configuration extending through a length of approximately 2 to 10 centimeters and preferably approximately 4 centimeters down to a diameter of less than 0.010 of an inch and preferably approximately 0.008 of an inch. The distal extremity of the core wire as represented by the portion 28c is of the 0.008 dimension. The outermost or distal extremity of the core wire is provided with a further tapered portion 28d having a length ranging from 1 to 3 centimeters and, preferably, approximately 2 centimeters in which the diameter tapers down from 0.008 to a suitable diameter such as 0.002 of an inch. The distal extremity of the core wire as represented by portion 28c has a length of approximately 0.5 centimeters and has a diameter of 0.002 inches.

An elongate flexible tubular member 31 formed of a suitable material such as plastic extends over a substantial portion of the core wire 28 from the control adapter 12 into a region near the distal extremity of the core wire. Thus as shown, the tubular member 31 has its proximal extremity flared outwardly to provide a cup-shaped portion 31a which forms a tight fit over a conical protrusion 32 provided as a part of the body 14. The portion 31a is clamped in place by a fitting 33 which is threaded onto a threaded portion 14a provided on the body 14. The tubular member 31 is of such a size so that there is space between the interior of the tubular member and the core wire 28.

The distal extremity of the tubular member 36 is provided with a balloon 36 which if desired can be formed integral with the tubular member 31. The balloon is in communication with the annular space (not shown) provided between the interior of the tubular member 31 and the exterior of the core wire 28. The distal extremity of the balloon 36 is bonded to the core wire 28 in a suitable manner so as to form a liquid tight seal. A suitable construction is disclosed in co-pending application Ser. No. 522,835 filed on Aug. 12, 1983 now U.S. Pat. No. 4,582,181. A flexible tip 41 can be provided on the distal extremity of the core wire 28 also in the manner described in co-pending application Ser. No. 522,835 filed on Aug. 12, 1983 now U.S. Pat. No. 4,582,181. It can be made of a suitable radiopaque material such as platinum so that the tip can be visualized during flouroscopy. An air bleed wire 42 can also be provided and can extend throught the side arm 18 of the control adapter 12 and can extend in the annular space provided between the interior of the tubular member 31 and the exterior of the core wire 28 and into the balloon 36 to facilitate bleediing air out of the balloon during the time that the balloon is being inflated with a radiopaque contrast liquid as described in co-pending application Ser. No. 522,835 filed on Aug. 12, 1983 now U.S. Pat. No. 4,582,181.

Means is provided for limiting the rotation of the core or guide wire 28 to no more than a predetermined number of turns and consists of a torque knob 51 formed out of a suitable material such as plastic. The torque knob 51 has a generally cylindrical configuration and is provided with a knurled surface 52. It is also provided with planar parallel surfaces 53 and 54 which adjoin the knurled surface 52. The torque knob 51 is provided with a cylindrical protrusion 56 which extends in a direction perpendicular to the surface 54. The protrusion 56 is sized so that it fits within a cylindrical bore 57 provided in the thumb screw 23. The proximal extremity of the core wire 28 extends through a small bore 58 provided in the cylindrical protrusion 56 and through the knurled knob 51 and is held in place by a set screw 59. The set screw 59 is threaded into a threaded bore 61 which extends radially of the knob 51 and through the bore 58 so that the set screw 59 can engage the core wire 58. In addition to ensure that the core wire is held in place, the core wire 28 is provided with an L-shaped portion 28a which is retained in a fixed position on the surface 53 by a large glob of suitable adhesive such as an epoxy which bonds the L-shaped portion 28a to the surface 53. A rotation limiter disc 62 is provided between the torque knob 51 and the thumb screw 23. It is provided with a bore 63 through which the cylindrical protrusion 56 extends. It is also provided with a protrusion 62a extending radially thereof. The protrusion 62a is adapted to be engaged by pins 64 and 66. Pin 64 extends in a direction which is parallel to the axis of the bore 57 and the thumb screw 23 and is offset from the center so that it is near the outer margin of the thumb screw. Similarly, the pin 66 extends inwardly in a direction parallel to the bore 58 in the torque knob 51 and also is spaced outwardly from the bore.

Retraction limiting means in the form of a retractor is provided for limiting any substantial movement of the torque knob 51 in a direction axially of the torque knob and consists of a generally cylindrical stop member 71. The stop member 71 is provided with a cutout 72 which is adapted to receive the side margin of the thumb screw 23. It is also provided with another cutout 73 which is adapted to accommodate the side margin of the torque knob 51. The stop member 71 is removably secured to the torque knob 51 by a cap screw 74. When the stop member 71 is in place, the lower extremity of the stop member engages the underside of the thumb screw 23 and therefore prevents the torque knob 51 from being retracted out of the thumb screw 23. It also ensures that the torque knob 51 will not pop out accidentally of the thumb screw 23. It will be noted that a portion that the stop member 71 is provided with portion 71a which extends beyond the surface 53 of the torque knob 51. It is provided with a a tapered or conical surface 76 so as to give a slightly rounded effect to the outer extremity of the stop member 71. This protrusion provided by the stop member 71 as hereinafter described can be readily engaged by a finger of the hand to facilitate rotation of the torque knob 51 and in effect provides fingertip control for the torque knob 51.

Operation and use of the low profile steerable dilatation catheter assembly with a rotation limiting device may now be briefly described as follows. As is well known to those skilled in the art in the use of dilatation catheters, dilatation catheters are conventionally used with guiding catheters (not shown). In use typically a guiding catheter is inserted into the coronary artery. The dilatation catheter shown in FIG. 1 is then introduced into the guiding catheter. Prior to introduction, the dilatation catheter 11 is prepared. An air bleed tube 42 is positioned in the dilatation catheter so that its distal end is near the distal extremity of the balloon 36. A radiographic contrast fluid is introduced into the balloon 36 through the side arm 17 to cause inflation of the balloon and at the same time expel any air through the vent tube 42. After the air has been expelled, the vent tube 42 can be bent into a U-shape and the open end inserted into the thumb screw 24 so as to form a seal. Thereafter, the radiographic contrast fluid is withdrawn from the balloon 36 to deflate the balloon 36.

The dilatation catheter assembly 11 then can be inserted into the guiding catheter (not shown) and advanced into the desired location by observing the same on a fluoroscope. The tip 41 before insertion of the catheter into the guiding catheter can be bent into a particular confirmation such as the one shown. After the dilatation catheter 11 has been inserted into the guiding catheter to facilitate forward advancement of the dilatation catheter 11, the torque knob 51 can be rotated in either a clockwise or counterclockwise direction to cause turning movement of the tip 41 to facilitate advancement of the tip of the arterial passages until the tip has been advanced sufficiently far so that the balloon 36 traverses or crosses the lesion which is to be dilated.

The balloon 36 of the dilatation catheter assembly 11 has a relatively low profile which facilitates advancement into very small openings in the artery, as for example, openings which have almost been substantially closed by the formation of plaque in the artery. Because of the torsional rigidity of the core or guide wire 28, movement of the torque knob 51 will cause rotational movement of the tip 41. It has been found that the torsional rigidity of the core or guide wire 28 is sufficient so that with two turns, each turn representing 360° rotation of the torque knob 51, the tip 41 will be rotated substantially 360°. As has heretofore been explained, means is provided for preventing the torque knob 51 from being rotated through an angle greater than two turns. This is accomplished by the use of the pins 64 and 66 engaging the protrusion 62a of the rotation limiter disc 62. In this connection it should be noted that the pins 64 and 66 leave their distal extremities spaced apart from each other. Alternatively, they can be offset radially from each other. In other words, they will clear each other when the torque knob 51 is rotated. Engagement only occurs when one of the pins 64 and 66 strikes the projection 62a. Let it be assumed that the thumb screw 23 and the torque knob 51 are positioned so that the pins 64 and 66 are lined up on opposite sides of the protrusion 62a. By rotating the torque knob 51 from the assumed position, one full revolution of the knob 51 can be accomplished before the projection 62a is engaged by the pin 64 on the thumb screw 23 and almost another complete revolution of the torque knob 51 can be accomplished before the pin 66 carried by it engages the protrusion 62a to inhibit any further rotation of the torque knob 51.

By limiting the rotation of the torque knob 51 so that it is less than approximately two revolutions, it is possible to prevent any substantial twisting of the balloon 36 and thereby prevent twisting to an extent which would make it difficult or impossible to inflate the balloon 36. Limiting the rotation of the torque knob 51 to two turns still makes it possible to obtain 360° rotation of the tip 41 of the dilatation catheter 11. During this 360° rotation of the tip 41, there is very little twisting of the balloon 36.

It should be appreciated that additional limited rotation can be provided by merely adding additional rotational limiter discs. Thus as shown in FIG. 4 in order to obtain substantially three revolutions of the torque knob 51 an additional limiter disc 81 has been provided which has a protrusion 81a. The protrusion 81a carries a pin 82 which is adapted to engage the protrusion 62a. The operation of this embodiment of the invention is very similar to that described for the previous embodiment with the exception that when the pins are all lined up, the torque knob 51 can be rotated through substantially three complete turns before the pins engage the protrusion 62a and 81a to stop further rotation of the torque knob. It has been found that at least three turns can be readily introduced into the catheter assembly 11 without danger of unduly twisting the balloon so as to inhibit its inflation.

During the rotation of the torque knob 51 it can be seen that the stop member 71 while permitting this rotation prevents the torque knob 51 from accidentally being pulled out of the thumb screw 23 or from being intentionally pulled out. In addition, the stop member 71 provides means adapted to be grasped by the finger to facilitate easy rotation of the torque knob 51.

Another embodiment of a steerable dilatation catheter assembly with a rotation limiting device is shown in FIGS. 5, 6 and 7. As shown therein, the catheter assembly 91 consists of an adapter 12 of the type which is utilized in the catheter assembly 11. A rotation limiting device 92 is mounted on the central arm 16 of the adapter 12. The rotation limiting device 92 includes a rotatable member 93 which is in the form of a cylindrical cap which is provided with a side wall 94 and a top or end wall 96. The side wall 94 is provided with circumferentially spaced outwardly facing recesses 97 extending longitudinally thereof which facilitate gripping of the outer surface 94 by hand during operation as hereinafter described. The top wall 96 is provided with a centrally disposed hole 98 which opens into a recess 99. The hole 98 opens into a centrally disposed bore 101 which extends through a centrally disposed cylindrical stem 102 concentric with the side wall 94. A cylindrical recess 103 is provided within the rotatable member 93.

The cap or housing which is formed by the rotatable member 93 is rotatably mounted upon an adapter 104 which is adapted to be mounted on the central arm 16 by suitable means such as an adhesive fit. The adapter 104 is provided with a truncated conical surface 106 which facilitates this mounting. The adapter is provided with a centrally disposed bore 107 which is adapted to receive the distal extremity of the stem 102. The adapter 104 is provided with an annular recess 108 which is adapted to carry suitable sealing means such as an O-ring 109. The O-ring 109 thus serves to form a liquid-tight seal between the adapter 104 and the stem 102 of the housing 93.

The guide wire 28 is adapted to extend through the bore 101 and to be inserted in the hole 98 and bent into the recess 99 after which suitable sealing means is provided such as an epoxy 111 which secures the end of the guide wire 28 in the recess 99. An outwardly extending protrusion 113 is provided on the top wall 96 and extends outwardly therefrom. It is adapted to be engaged by a finger of a hand to facilitate rotation of the rotatable member 93. The proximal extremity of the guide wire 28, since it is secured to the rotatable member, will be rotated with the rotatable member.

Means is provided in the rotation limiting device for limiting the rotation to no more than a predetermined number of turns as, for example, four complete turns or revolutions. This means consists of a plurality of discs 116 which are disposed within the recess 103 as, for example, the three discs shown in FIG. 7. The discs 116 can be substantially identical. Each of the discs 116 is provided with a central bore 117 and a arcuate recess 118 which is generally concentric with the bore 117. The arcuate recess 118 extends through substantially 360° except for a small web 119. Each disc has a downwardly extending cylindrical protrusion 121 which is adapted to seat in and travel in the arcuate recess 118 provided in the disc there below. The protrusion 121 of the lowermost disc is adapted to seat in an arcuate recess 123 provided in the adapter 104. The recess 123 is similar to the recesses 118 and extends through substantially 360° except for a small web 124. The rotatable member 93 is provided with a downwardly extending protrusion 125 extending downwardly from the top wall 96 and which is adapted to seat in the arcuate recess 118 of the uppermost disc 116.

In assembling the rotation limiting device, the discs are inserted into the housing-like rotatable member 93 so that the uppermost disc has the protrusion 125 in its recess 118 and so that the protrusions 121 provided in the discs are disposed in the recesses 118 of the discs below. A retainer 126 is provided for retaining the adapter 104 within the lower extremity of the housing-like rotatable member 93 and is provided with a central opening 127 and an upstanding outer rim 128. The retainer 126 is adapted to engage but rotate freely with respect to the shoulder 129 of the adapter 104 and to have the rim 128 bonded to the outer lower extremity of the housing-like rotatable member 93 by suitable means such as adhesive. When assembled in this manner, the various parts of the rotation device are held together in a unitary assembly while still permitting rotation of the housing 93 relative to the adapter 104 through a predetermined number of revolutions as, for example, approximately 4. The number of revolutions is determined by the number of discs and the number of arcuate slots which are provided. As can be seen there are three slots 118 provided in the three discs 116 and another arcuate slot 123 is provided in the adapter 104.

Thus it can be seen that there has been provided a catheter assembly with a rotation limiting device which has an attractive appearance which is relatively simple to fabricate and assemble. It also provides for the maximum desired number of rotations for the guide wire.

It is apparent from the foregoing that there has been provided a low profile steerable dilatation catheter of the type which limits twisting movement of the balloon while at the same time providing sufficient torsional rigidity so that there is at least 360° rotation of the tip of the dilatation catheter and therefore it does not detract from the capabilities of the dilatation catheter. The additional torsional rigidity required in the catheter assembly to obtain the 360° rotation of the tip of the catheter assembly with no more than two turns of the torque knob can be readily accomplished. The dilatation catheter is also of the type which can be readily manufactured and assembled.

What is claimed is:

1. In a steerable dilatation catheter assembly, an adapter having at least one arm, a guide wire having proximal and distal ends with the proximal end extending through the adapter, a flexible tubular member having one end secured to the adapter and extending over the guide wire and having a balloon carried by a distal portion thereof, the distal extremity of the balloon being bonded to the guide wire to form a liquid-tight seal between the guide wire and the balloon, a flexible tip secured to the guide wire and means secured to the guide wire and carried by the arm for limiting the rotation of the guide wire through a number of turns less than a predetermined number of turns to prevent undue twisting of the balloon.

2. An assembly as in claim 1 wherein said means for limiting the rotation of the guide wire includes a rotatable member, means securing the guide wire to the rotatable member and means engaging the rotatable member for preventing rotation of the rotatable member for more than a predetermined number of turns.

3. An assembly as in claim 2 wherein said means for preventing rotation of the rotatable member more than a predetermined number of turns includes a plurality of superposed discs, each of the discs including cooperative protrusion and recess means.

4. In a steerable dilatation catheter assembly, an adapter having at least one arm, a guide wire having proximal and distal ends with the proximal end extending through the adapter, a flexible tubular member having one end secured to the adapter and extending over the guide wire and having a balloon carried by a distal portion thereof, the balloon having a distal extremity, the distal extremity of the balloon being bonded to the guide wire to form a liquid-tight seal between the guide wire and the balloon, a flexible tip secured to the guide wire and means secured to the guide wire and carried by the arm for limiting the rotation of the guide wire through a number of turns less than a predetermined number of turns, said means for limiting rotation of the guide wire including a rotatable member, means securing the guide wire to the rotatable member and means engaging the rotatable member for preventing rotation of the rotatable member for more than a predetermined number of turns including a plurality of superposed discs, each of the discs including cooperative protrusion and recess means, said rotatable member being in the form of a housing having a cylindrical recess therein, said discs being disposed in said cylindrical recess.

5. In a steerable dilatation catheter assembly, an adapter having at least one arm, a guide wire having proximal and distal ends with the proximal end extending through the adapter, a flexible tubular member having one end secured to the adapter and extending over the guide wire and having a balloon carried by a distal portion thereof, the distal extremity of the balloon being bonded to the guide wire to form a liguid-tight seal between the guide wire and the balloon, a flexible tip carried by the guide wire, means secured to the guide wire and carried by the arm for rotating the guide wire and means for limiting the rotation of the guide wire at the proximal end to less than approximately four turns, the guide wire having sufficient torsional rigidity so that with the use of said turns, the tip will be rotated through substantially 360° while preventing undue twisting of the balloon.

6. A dilatation catheter as in claim 5 wherein a major portion of said guide wire has a diameter in excess of 0.013 of an inch.

7. A dilatation catheter as in claim 5 wherein said means for causing rotation of said guide wire includes a thumb screw mounted in said one arm and having a guide wire extending therethrough the means carried in said one arm and engaged by the thumb screw for forming a liquid-tight seal between the guide wire and said one arm, a torque knob rotatably mounted in the thumb screw and having the guide wire secured thereto so as the torque knob is rotated the guide wire is rotated and means disposed between the torque knob and the thumb screw for limiting rotational movement of the torque knob with respect to the thumb screw to at least approximately two turns.

8. A dilatation catheter as in claim 7 together with a stop member carried by the torque knob, said stop member being positioned so that it is adapted to engage the thumb screw to prevent movement of the torque knob axially of the thumb screw beyond a predetermined distance.

9. A catheter assembly as in claim 8 wherein said stop member includes a protrusion extending above the torque knob to facilitate rotation of the torque knob.

10. A catheter assembly as in claim 7 wherein said means disposed between said torque knob and said thumb screw includes a rotation limiter disc, said rotation limiter disc having a radially extending protrusion carried thereby and pins carried by said torque knob and said thumb screw and being positioned so that they are adapted to engage the protrusion of the rotation limiter disc as the torque knob is rotated.

11. A catheter assembly as in claim 7 wherein said means disposed between said torque knob and said thumb screw includes first and second rotation limiter discs having radially extending protrusions, and pin carried by at least one of said protrusions adapted to engage the protrusion of the other rotation limiter disc and pins carried by the torque knob and the thumb screw and adapted to engage the protrusion of a rotation limiter disc.

12. A catheter assembly as in claim 5 wherein said control adapter is provided with two additional arms together with a bleed wire extending through one of the two additional arms, the other of the two additional arms being adapted to receive a radiopaque contrast liquid into the balloon for inflating the balloon.

13. A catheter assembly as in claim 5 wherein a major portion of the guide wire has a diameter of approximately 0.016 of an inch, wherein an intermediate distal portion of the guide wire has a diameter of approximately 0.008 of an inch and wherein the extreme distal portion of the guide wire has a dimension of approximately 0.002 of an inch.

14. In a rotation limiting device for use with a steerable dilatation catheter having an adapter with at least one arm, a guide wire having proximal and distal ends with the proximal end extending through the adapter, a flexible tubular member having one end secured to the adapter and extending over the guide wire and having a balloon carried by the distal portion thereof, the balloon having a distal extremity which is bonded to the guide wire to form a liquid-tight seal between the guide wire and the balloon and a flexible tip secured to the guide wire, the rotation limiting device comprising a rotatable member, means adapated to secure the guide wire to the rotatable member, and means including a plurality of superposed discs engaging the rotatable member for preventing rotation of the rotatable member for more than a predetermined number of times, each of said discs including cooperative protrusion and recess means.

15. A device as in claim 14 wherein said rotatable member is in the form of a housing having a cylindrical recess therein and wherein said discs are disposed in said cylindrical recess.

16. A device as in claim 15 together with an adapter and wherein the housing and the adapter each are provided with a cooperative means to cooperate with the discs.

17. A device as in claim 16 wherein each disc is provided with a recess extending through substantially 360° and a protrusion which is adapted to seat in the recess of another disc.

18. A device as in claim 15 wherein said housing is provided with a stem and in which the discs are rotatably mounted on the stem.

* * * * *